United States Patent [19]

Janata

[11] Patent Number: 5,227,134
[45] Date of Patent: Jul. 13, 1993

[54] DYNAMIC IMMUNOCHEMICAL AND LIKE CHEMICAL SPECIES SENSOR APPARATUS AND METHOD

[76] Inventor: Jiri Janata, No. 606, 111 S. 1100 East, Salt Lake City, Utah 84102

[21] Appl. No.: 737,432

[22] Filed: Jul. 29, 1991

[51] Int. Cl.$^5$ .......................................... G01N 21/64
[52] U.S. Cl. ............................. 422/82.08; 422/82.06; 422/82.07; 422/82.11; 436/172
[58] Field of Search ............... 422/82.06, 82.07, 82.08, 422/82.11; 436/172, 532, 535; 250/458.1, 461.1, 459.1; 356/318, 419; 128/670, 634

[56] References Cited

U.S. PATENT DOCUMENTS

| | | | |
|---|---|---|---|
| Re. 31,879 | 5/1985 | Lubbers et al. | 436/133 |
| 4,548,907 | 10/1985 | Seitz et al. | 422/82.07 |
| 4,557,900 | 12/1985 | Heitzmann | 422/55 |
| 4,582,809 | 4/1986 | Block et al. | 250/458.1 |
| 4,666,672 | 5/1987 | Miller et al. | 436/172 |
| 4,822,746 | 4/1989 | Walt | 436/172 |
| 4,892,383 | 1/1990 | Klainer et al. | 422/82.06 |
| 4,895,809 | 1/1990 | Schlabach et al. | 436/172 |
| 4,929,561 | 5/1990 | Hirschfeld | 422/82.07 |
| 5,081,041 | 1/1992 | Yafuso et al. | 422/82.06 |
| 5,096,671 | 3/1992 | Kane et al. | 128/634 |

*Primary Examiner*—Robert J. Warden
*Assistant Examiner*—Hien Tran
*Attorney, Agent, or Firm*—Thorpe, North & Western

[57] ABSTRACT

An immunochemical sensor for measuring the concentration of immunochemical species in a first solution includes a light-emitting element for exciting fluorescent particles which collide with the surface of the element to cause the particles to, in turn, emit light, where the surface includes first immunoreagents coupled thereto, and a light detector for detecting the light emitted by the particles, where the amount of light detected is dependent upon the elasticity of collision of the particles from the surface of the light-emitting element—more light detected for less elastic collisions. A membrane at least partially surrounds the light-emitting element and includes a second solution which is maintained in contact with the light-emitting element. The membrane allows the passage therethrough of the immunochemical species to be detected while prohibiting passage therethrough of other species. The light-emitting element and membrane are immersed in the first solution to allow measuring the concentration of the immunochemical species. Fluorescent particles are included in the second solution in the membrane and some of the particles have second immunoreagents covalently attached thereto, the second immunoreagents being bindable to the first immunoreagents upon contact therewith. With this configuration, the concentration of immunochemical species comprising either the first or second immunoreagents may be measured by measuring the light intensity of particles colliding with the surface of the light-emitting element which, in turn, provides a measure of the average elasticity of collision of the particles from the surface and this is proportional to the concentration of the immunochemical species to be detected.

9 Claims, 3 Drawing Sheets

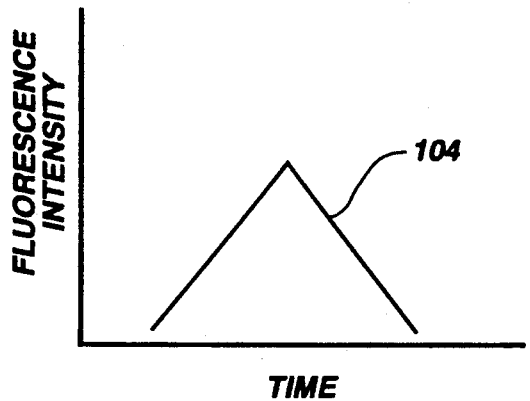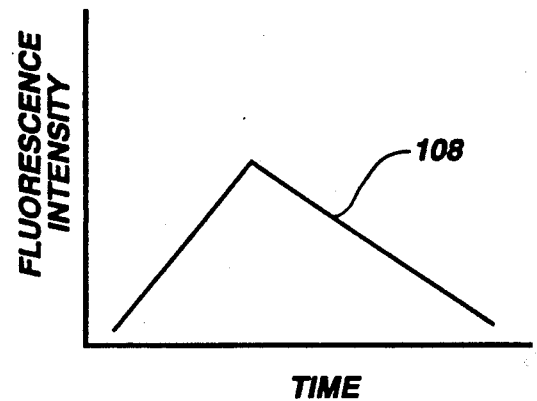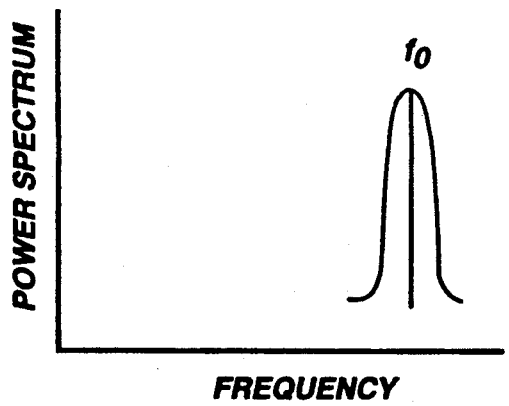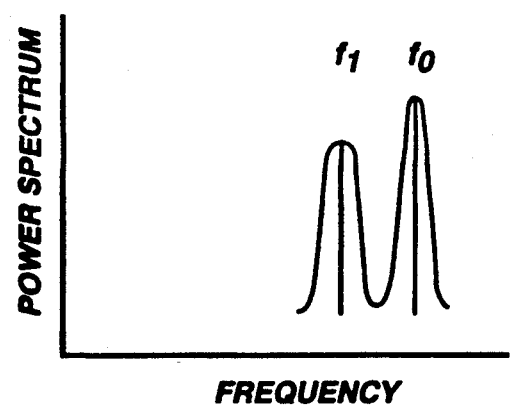
Fig. 2A                Fig. 2B

DYNAMIC IMMUNOCHEMICAL AND LIKE CHEMICAL SPECIES SENSOR APPARATUS AND METHOD

BACKGROUND OF THE INVENTION

This invention relates to a method and apparatus for detecting the concentration of chemical species in a solution such as the concentration of immunochemical species.

Accurate, more precise methods of detecting the presence and concentration of various chemical species in a solution, both in vivo and in vitro, have been the subject of much research and numerous development efforts. See, for example, U.S. Pat. Nos. 3,966,580, 3,574,062, 3,843,446, 3,999,122, 3,831,432 and 4,238,757.

As explained in the above-cited patents, detecting the presence and concentration of chemical species in a solution requires that the chemical sensor exhibit selectivity, i.e., the ability to detect a particular chemical species to the exclusion of others. Immunochemical reactions, by their nature, are highly selective in that certain immunochemical species, e.g., antibodies, react or bond to only certain other immunochemical species, e.g., antigen. Because of this selectivity characteristic, numerous attempts have been made to develop direct chemical sensors for sensing various immunochemical species. See, for example, Janata, J., *Principles of Chemical Sensors*, Plenum Publishing Co., New York, New York, 1989. These attempts, however, have generally been unsuccessful for the following reasons: (1) selective bonding between the antibody and corresponding antigen or hapten (low molecular weight antigen) is progressive in that the strength of the bond between the immunochemical species increases with time—as a result, this bond eventually becomes so strong that a permanent antibody/antigen complex is formed and so the interaction becomes irreversible and continued detection or sensing is prevented; and (2) a reliable transduction mode is not known for direct immunochemical reactions (transduction, in this context, means conversion or transformation of the chemical bonding event into a measurable physical signal).

SUMMARY OF THE INVENTION

It is an object of the invention to provide a new and improved method and apparatus for efficiently and accurately detecting the presence and concentration of various chemical species, such as immunochemical species, in a solution.

It is also an object of the invention to provide such a method and apparatus in which the detection may be made very rapidly and accurately.

It is a further object of the invention to provide such a method and apparatus which avoids the difficulty of irreversibility of immunochemical reactions.

It still another object of the invention to provide such a method and apparatus which employs a suitable transduction mode for measuring the presence and concentration of chemical species especially in immunochemical reactions.

The above and other objects of the invention ar realized in a specific illustrative embodiment of an immunochemical sensor for measuring the concentration of immunochemical species in a solution. The sensor includes a light developing element having a surface area in which the light excites fluorescent particles which collide with the surface area to cause the particles to emit light whose signatures are dependent upon the elasticity of collision of the articles. The surface area includes first immunoreagents coupled thereto. The sensor also includes a light detector for detecting light emitted from the particles and for producing a measure of the average elasticity of collision of the particles. A membrane is provided to at least partially surround the light developing element and for allowing the passage therethrough of the immunochemical species when the membrane and light developing element are disposed in a solution containing the species. Fluorescent particles are disposed in a second solution held in the membrane, and at least some of the particles include second immunoreagents coupled thereto. The second immunoreagents are bindable to the first immunoreagents upon contact therewith.

When the immunochemical species to be detected is either the first or second immunoreagents, a high concentration of the immunochemical species in the first solution will result in frequent binding of the species either with the immunoreagent on the surface area or the immunoreagent on the particles. The result of this is that more bonding sites of the immunoreagents are occupied so that less bonding will occur between the first and second immunoreagents when particles collide with the surface area; if less bonding occurs (to hold the colliding particles onto the surface area), more particles will rebound in an elastic way so that the detected light emitted by the particles, and in particular the detected light signatures, will have a certain characteristic. On the other hand, if the concentration of the immunochemical species is low, fewer of the species will bind either to the immunoreagents on the particles or the immunoreagents on the surface area, leaving more bonding sites available between the first and second immunoreagents so that more bonding will occur therebetween upon collision of the particles with the surface area. If more bonding occurs, then less rebounding of particles will occur so that the rebounding will appear more inelastic and this will cause the light detector to detect light emitted by the particles, that is, the light signatures; these detected light signatures will have a different characteristic than that when the rebounding is more elastic. In this manner, the variation in light detection is dependent upon the variation in average elasticity of collision of the particles and this, in turn, provides a measure of the concentration of the immunochemical species in the solution.

The transduction mode employed in the abovedescribed illustrative embodiment of measuring elasticity of the collisions between particles and a surface area by measuring light emission, provides an efficient and accurate method of detecting the concentration of various immunochemical species. The difficulty of the irreversibility of immunochemical reactions is avoided since the bonds formed on collision of the particles with the surface area of the sensor are not permanent but rather are immediately disrupted by the mechanical motion of the particle rebounding from the surface. The degree of elasticity exhibited in this rebounding, however, varies and it is this variation which is utilized to make the desired measurement.

BRIEF DESCRIPTION OF THE DRAWINGS

The above and other objects, features and advantages of the invention will become apparent from a consideration of the following detailed description presented in connection with the accompanying drawings in which:

FIGS. 2A and 2B show fluorescent intensity graphs and power spectrum graphs of elastic and less elastic fluorescent particles respectively, rebounding from a surface area at which the fluorescent light intensity is detected.

DETAILED DESCRIPTION

In order to understand the operation of the present invention, two phenomena should be understood, these being the emission of light from a fluorescent colloid particle rebounding from a surface area about which there is an evanescent field of light, and the elasticity and inelasticity of such particles in rebounding from the surface area. These two phenomena, which are utilized in the present invention, will be explained in conjunction with the description of the immunochemical sensor shown diagrammatically in FIG. 1.

Figure 1:
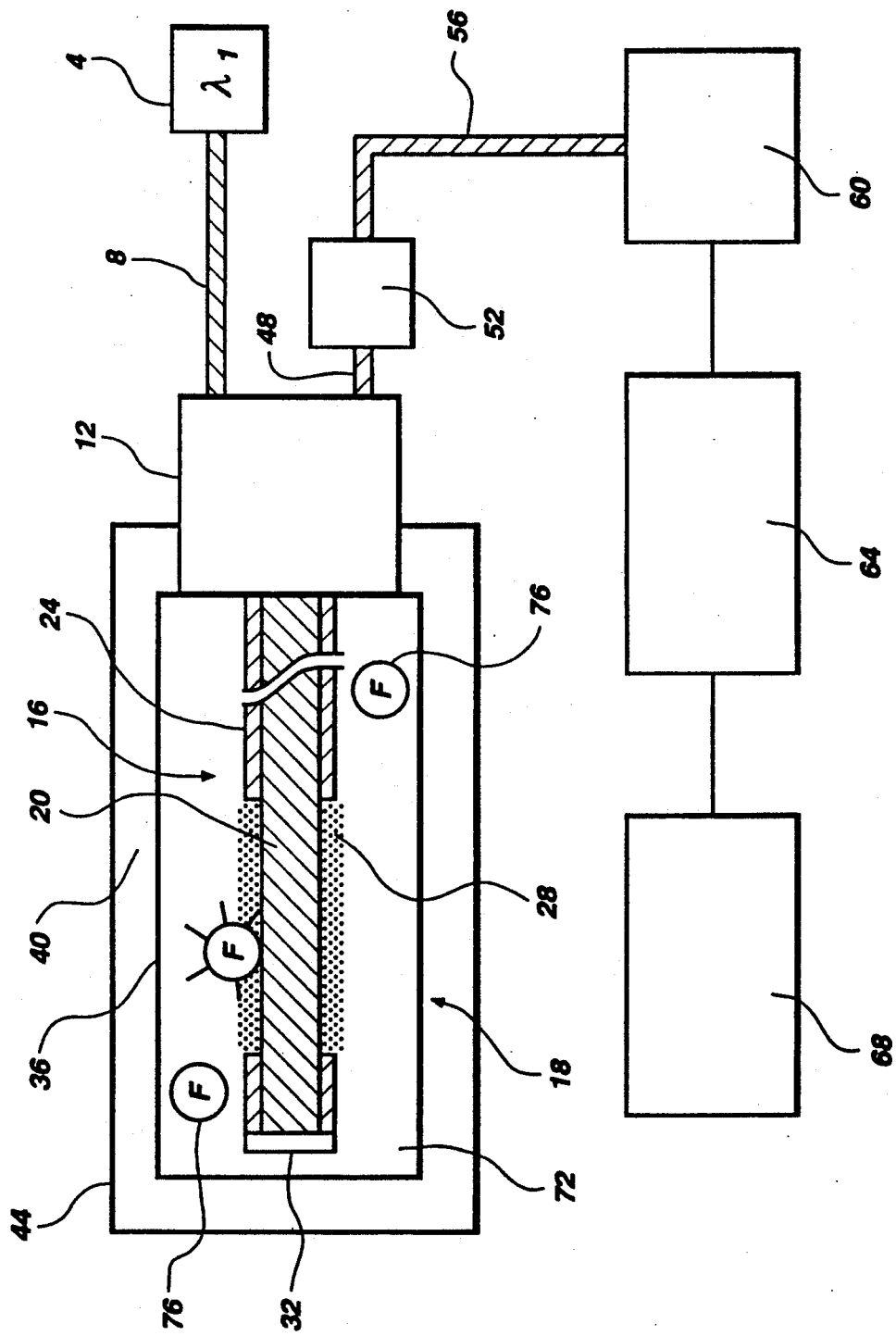
FIG. 1 is a diagrammatic representation of an immunochemical species sensor made in accordance with the principles of the present invention.

The sensor of FIG. 1 includes a source 4 of light having a wavelength $\lambda_1$ (e.g. 4000 angstroms). This light is supplied via a light transmitting conduit 8, such as an optical waveguide or optical fiber, to an optical coupler 12. The optical coupler 12, in turn passes the light to another optical waveguide 16 which is part of a probe 18. The waveguide 16 includes a centrally disposed light-transmitting material 20, such as plastic or glass, partially coated with a light reflective material 24 such as a highly reflective metal. A portion of the light-transmitting material 20 is left exposed, as shown in FIG. 1, to produce an evanescent field of light 28 which extends some distance radially from the light-transmitting material. A light-reflecting cap 32 is disposed over the end of the light-transmitting material 20 to reflect light back toward the optical coupler 12.

The waveguide 16 is surrounded by a dialysis membrane 36 which allows selected immunochemical species to pas therethrough while preventing the passage of other species. Such immunochemical species would be contained in a solution 40 held in a container 44 into which the waveguide 16 and membrane 36 would be disposed for the purpose of detecting the presence and concentration of the immunochemical species. The membrane 36 might illustratively be cuprophane or acetyl cellulose and the immunochemical species to be detected might illustratively be digoxin, an antigen.

The optical coupler 12 is also coupled by way of an optical waveguide 48 to a filter 52 which passes light having a wavelength $\lambda_2$ (e.g. 5200 angstroms) but blocks out light of other wavelengths including that with wavelength $\lambda_1$. The filter 52 is coupled by way of an optical waveguide 56 to a photomultiplier 60 or other suitable light-to-electricity converter. Light which is passed by the filter 52 to the photomultiplier 60 is converted to an electrical signal whose magnitude is proportional to the intensity of the light (which varies over time) received from the filter, and such electrical signal is supplied to a spectrum analyzer 64 which analyzes the signal and produces a power spectrum showing the intensity of the light detected as a function of frequency. This, in turn, represents the average elasticity of particles (means coefficient of restitution) colliding with the surface of the light-transmitting material 20, as will be discussed later.

The information produced by the spectrum analyzer 64 is displayed by the display unit 68 to provide an indication of a concentration of immunochemical species in the solution 40 contained in the container 44.

Detection of the concentration of the immunochemical species migrating through the dialysis membrane 36 utilizes the two phenomena referred to earlier by providing a solution, such as a saline solution, 72 within the membrane 36 containing a suspension of colloid particles 76. These particles, which might illustratively be uniform Latex particles such as produced by Serodyne, Inc. or Fluoresbriter TM microparticles produced by Polysciences, Inc., carry covalently bonded fluorophores which absorb light of wavelength $\lambda_1$ and which, when excited, emit fluorescent light of wavelength $\lambda_2$. The particles 76 are excited to emit light when they enter the evanescent field of light 28. Entry into this field by the particles results by the particles moving either as a result of Brownian motion or as a result of forced convection caused, for example, by agitating or stirring. The particles thus randomly collide with the surface of the light-transmitting material 20 exposed through the light reflective material 24.

The fluorescent light emitted by the fluorophores is collected by the light-transmitting material 20 and guided back to the optical coupler 12 and then passed through the filter 52 which, as already indicated, passes light of wavelength $\lambda_2$. The fluorescent light ultimately is passed to the photomultiplier 60 where it is converted to an electrical signal as previously described.

The amount of fluorescent light collected by the waveguide 16 is dependent upon the elasticity of the particles 76 and thus the degree to which the particles will rebound from the surface of the light-transmitting material 20. If the particles are completely elastic, the restitution coefficient (ratio of the inbound and outbound velocity) is close to unity. On the other hand, if some binding or adhesion occurs when the particles collide with the surface of the light-transmitting material 20, the outbound velocity of the particles is decreased because some of the original kinetic energy would have been lost upon impact and of course the resident time of the particles on the surface would increase. In such case, the value of the restitution coefficient is greater than 1 to reflect the non-elastic nature of the particle/surface interaction.

Emission of fluorescent light by particles colliding with the surface of the exposed waveguide 16 (FIG. 1) is illustrated in FIGS. 2A and 2B, where FIG. 2A shows at the top a time-varying optical signal whose kinetics (shape) represents a restitution coefficient of 1. That is, the fluorescent light intensity resulting from a single elastic collision is represented as an isosceles triangle 104 with the peak of the triangle (intensity) corresponding in time to the impact of the particle with the surface area of the waveguide. The top graph of FIG. 2B represents the fluorescent light intensity resulting from an inelastic collision by a particle 76 with the exposed surface of the waveguide 16, and as shown, the intensity representation is a skewed triangle 108 in which the time during which light is detected at the waveguide is greater when the particle is outbound (decreasing portion of triangle) than when the particle is inbound (increasing portion of triangle). Clearly, the detected fluorescent light intensity varies with variation in the elasticity of the particles striking the exposed portion of the light waveguide.

It is known that many identical events having the same or similar kinetics may be characterized by a frequency which is unique for the kinetics of that event in the time domain. Thus, for multiple collisions of colloid particles having an elastic restitution coefficient (unity) a unique peak at frequency of $f_0$ (lower graph of FIG. 2A) in the power spectrum represents the event. The power spectrum, as mentioned earlier, is a plot of the distribution of the intensity of the fluorescent light as a function of frequency. For collisions of other particles with an inelastic restitution coefficient, a power spectrum with frequencies of $f_0$ and $f_1$ (lower graph of FIG. 2B) results. The relative amplitude of these peaks depends upon the number of inelastic versus elastic collisions and, as will be discussed momentarily, this information may be utilized to determine the concentration of an immunochemical species in a solution. In particular, the amplitude at frequency peak $f_1$ represents the light signature for inelastic collisions, while the amplitude of the frequency peak $f_0$ represents the light signature for elastic collisions, and so the relative amplitude of the two peaks is a measure of the average elasticity of collisions of the particles. As earlier indicated, power spectra such as shown as the lower graph in FIG. 2B are produced by the spectrum analyzer 64 of FIG. 1 for display on the display unit 68, also shown in FIG. 1. The spectrum analyzer 64 produces the power spectra by performing Fourier transformations from the time domain to the frequency domain of the fluctuations of optical intensity of the fluorescent light of wavelength $\lambda_2$, represented by the electrical signal developed by the photomultiplier 60 (FIG. 1), all in a well-known manner.

Figure 3A:
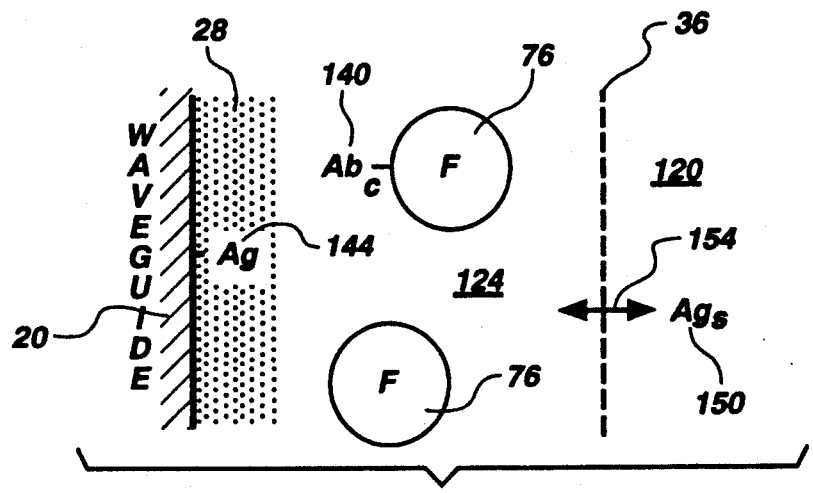
FIGS. 3A, 3B and 3C show diagrammatically three embodiments of the immunochemical sensing process of the present invention.
Figure 3B:
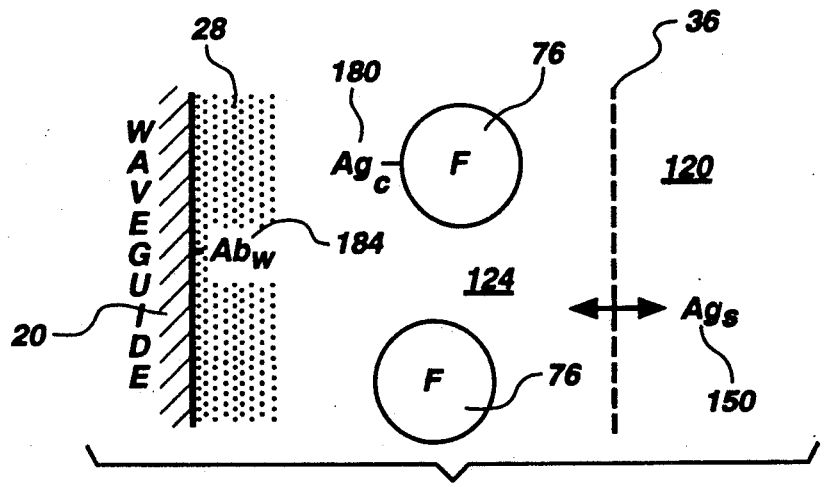
Figure 3C:
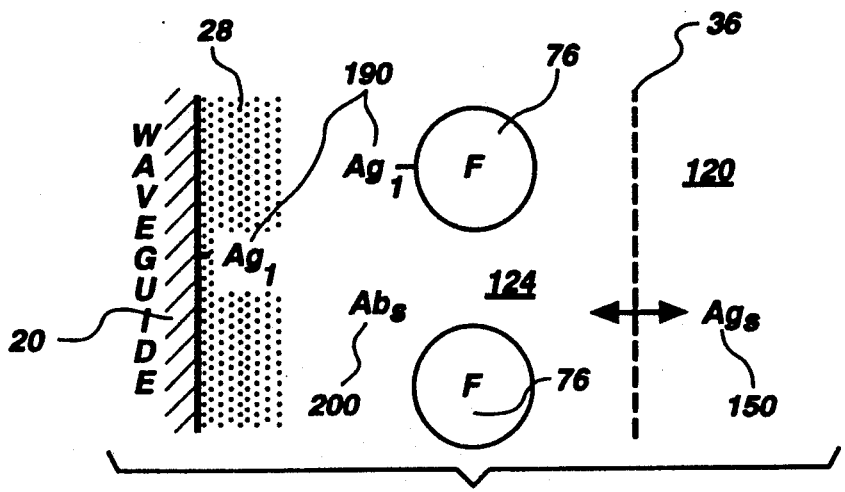

FIGS. 3A, 3B and 3C diagrammatically represent three embodiments of immunochemical sensing processes which may be carried out with the sensor shown in FIG. 1. All three embodiments utilize the availability of immunospecific interactions between two solid surfaces. These reactions are effectively reversible so that the typical irreversibility of immunochemical reactions is avoided. Also, in all three embodiments, fluorescent immunochemically non-modified particles 76 are added to the solutions into which the immunochemical species to be detected will migrate via the dialysis membrane 36. Light emitted from these particles (elastic collisions) provides a signal which serves as the frequency reference $f_0$, whereas light emitted from particles modified by attaching an immunoreagent provide signals which serve as both the reference frequency $f_0$ and the signal frequency $f_1$ (since some collisions are elastic and some are inelastic.

Referring to FIG. 3A, the immunochemical species to be detected is a soluble antigen $Ag_s$ 150. The arrow 154 illustrates the migration of the antigen 150 from a solution sample 120 containing the antigen through a dialysis membrane 36 into a solution 124 contained within the membrane 36 and in which the fluorescent particles 76 have been added. Some of the fluorescent particles 76 include covalently bonded immobilized antibodies $Ab_c$ 140. Covalently bound to the surface of light-transmitting material 20 is immobilized antigen Ag 144.

As the soluble antigen 150 migrates through the membrane 36 to the solution 124, many bond with the antibodies 140 on the fluorescent particles 76 and, of course, with the greater concentration of soluble antigen, more bonding with the antibodies will occur. As already indicated, as a result of Brownian motion or through mechanical agitation, the particles 76 are caused to collide with the surface of the light-transmitting material 20 and rebound therefrom. For those particles 76 which either have no antibodies 140 bonded thereto or which include antibodies 140 bonded with soluble antigen 150, the rebounding of the particles from the surface of the light-transmitting material 20 is essentially elastic. However, for those particles 76 including only an attached antibodies 140, many of such particles come in contact with a site on the surface of the light-transmitting material 20 occupied by immobilized antigen 144 to temporarily form a bond and slow the rebound of the particle from the surface. Thus both elastic and inelastic collisions are occurring on the surface of the light-transmitting material 20 and the average elasticity of collision of the particles depends upon the 150 and this, as already indicated, depends upon the concentration of the antigen. Thus, with a high concentration of antigen 150, more of the antigen will bind with antibodies 140 on the particles 76 and so fewer particles will be slowed in rebounding from the surface of the light-transmitting material 20 (since the antibodies 140 on the particles 176 10 will already be bound to an antigen 150 making it impossible to temporarily bond with antigen 144 on the surface). Thus, the greater the concentration of soluble antigen 150, the greater will be the average elasticity of rebound and this is measurable as previously described to indicate the concentration of soluble antigen.

As earlier indicated, the antigen to be detected might illustratively be digoxin, with the antibody attached to the fluorescent particles 76 being the monoclonal antibody to digoxin. Of course, other bondable antibodies and antigens could be utilized as could other non-immunochemical species having the capability of bonding together.

FIG. 3B also illustrates a process for detecting the concentration of a soluble antigen 150, but in this case immobilized antigen $Ag_c$ 180 is covalently attached to the fluorescent particles 76 (at least some of the particles) and immobilized antibody Abw 184 is covalently attached to the surface of the light-transmitting material 20. In this embodiment, some of the soluble antigen 150, which is to be detected, binds with some of the antibodies 184 to thus take up what would otherwise be binding sites for the immobilized antigen 180 attached to the particles 76. Of course, the greater the concentration of soluble antigen 150, the greater are the number of sites occupied by the antigen on the surface of the light-transmitting material 20. With fewer sites for the immobilized antigen 180 to bind with on the surface of the light-transmitting material 20, the greater is the number of particles which will rebound from the surface in an elastic fashion and thus greater is the average elasticity of rebound. The average elasticity of the collision, represented by the relative amplitude of the power spectrum plots, thus provides an indication of the concentration of soluble antigen 150.

FIG. 3C illustrates still another embodiment of the process of the present invention in which, again, weak soluble antigen 150 is the immunochemical to be detected. In this case, a strong antigen Ag 190 is attached both to the surface of the light-transmitting material 20 and to some of the fluorescent particles 76. There is also dissolved in the solution 124 contained within the dialysis membrane 36 a soluble antibody $Ab_s$ 200 as shown.

The weak soluble antigen 150 enters through dialysis membrane 36 and binds with some of the soluble antibodies 200. Some of the antibodies 200 also bind with the strong antigen located either on the surface of the light-transmitting material 20 or on the fluorescent particles 76 which then allows the particles to temporarily bind with the surface of the light transmitting material in a type of $Ag_1 Ab_s Ag_1$ sandwich bond. If the concentration of soluble antigen 150 is greater, more of the soluble antibodies 200 will be taken up in bonds with the soluble antigen and thus fewer of the fluorescent particles 76 will be able to temporarily bind with the surface of the light-transmitting material 20. That is, more of the particles will rebound elastically from the surface so that the average elasticity of collision of the particles is greater which, as already discussed, indicates a greater concentration of the immunochemical species to be detected.

In all of the embodiments of FIGS. 3A, 3B and 3C, the collisions of the fluorescent particles with the surface of the light-transmitting material 20 are more elastic if the concentration of soluble antigen 150 is high, and more inelastic if the concentration is low. For this detection process to be effective, it needs to be reversible, otherwise the surface of the light-transmitting material of the sensor would become covered with permanently attached immunochemical species bonded together. T provide this feature of reversibility the primary bond between immunochemical species at this surface must be disrupted by the kinetic energy of the colliding colloidal particles, before secondary bonds can be formed. Prevention of such permanent attachment can be achieved by reducing the binding site density (available sites for permanent attachments to occur), increasing the temperature of the solution to thereby increase the kinetic energy of the fluorescent particles, and stirring or otherwise agitating the solution to thereby effectively increase the mechanical disruptive force of the particles.

Calibration of the apparatus shown in FIG. 1 may be carried out by first causing the covalent bonding of selected immunochemical species to a known proportion of fluorescent particles 76 in the solution 72. The probe 18 of FIG. 1 is then immersed successively in solution samples containing known concentrations of soluble antigen. As the antigen penetrates through the dialysis membrane and some bind to the antibody binding sites either on the fluorescent particles or surface of the light-emitting element, the power spectra of the fluctuating fluorescent light emissions are recorded and the difference between the amplitude of the reference frequency (representing elastic collisions) and the amplitude of the frequency representing inelastic collisions is plotted against the known concentration of soluble antigen. The plot provides a calibration curve so that the concentrations of unknown samples may be read from the curve by the spectrum analyzer 64.

It is to be understood that the above-described arrangements are only illustrative of the application of the principles of the present invention. Numerous modifications and alternative arrangements may be devised by those skilled in the art without departing from the spirit and scope of the and the appended claims are intended to cover such modifications and arrangements.

What is claimed is:

1. A chemical sensor for measuring the concentration of a chemical species in a sample comprising means having a surface area for developing light for exciting fluorescent particles which collide with the surface area to cause the particles to emit light whose signatures at the surface area are dependent upon an elasticity of collision of the particles, said surface areas including first reagents coupled thereto, wherein said light developing means comprises means for producing an evanescent field of light into which the particles enter when they collide with the surface area, and for collecting the emitted light from the particles, means for detecting the light emitted by the particles to produce a measure of an average elasticity of collision of the particles, a membrane means at least partly surrounding the light developing means for disposition in a sample, and for allowing passage therethrough of a chemical species in said sample, a solution disposed within the membrane means, and fluorescent particles disposed in the solution with access to the light developing means, at least some of which include second reagents coupled thereto, said second reagents being bindable to the first reagents upon contact, wherein said particles include fluorophores for absorbing light of wavelength $\lambda_1$ and for emitting light of wavelength $\lambda_2$ when excited by light from the light developing means, wherein said chemical species comprises either the first or second reagent, and wherein the average elasticity of collision of the particles from the surface area is proportional to the concentration of said chemical species in the sample.

2. A sensor as in claim 1 wherein said light developing means comprises an optical fiber, and means for supplying light to the optical fiber.

3. A sensor as in claim 1 wherein said light developing means comprises an optical waveguide, and means for supplying light to the waveguide.

4. A sensor as in claim 3 wherein said light detecting means comprises means for converting the light of wavelength $\lambda_2$ to an electrical signal whose magnitude varies over time and is proportional to the intensity of the converted light, and means for displaying a representation of the electrical signal to indicate the average elasticity of collision of the particles and thus the concentration of chemical species in the sample.

5. A sensor as in claim 4 wherein said light developing means comprises a source of light of wavelength $\lambda_1$ and means for transmitting such light to the surface area, and wherein said light detecting means further includes filter means for receiving the collected light and for passing light of wavelength $\lambda_2$ to the converting means and for blocking light of other wavelengths, and optical coupler means for transferring light from the source of light to the transmitting means and for transferring collected light to the filter means.

6. A sensor as in claim 4 wherein said displaying means comprises means for Fourier transforming the electrical signal from time domain to frequency domain, and means for displaying the transformed signal as a power spectrum representing a plot of distribution of the intensity of light of wavelength $\lambda_2$ which, in turn, represents the average elasticity of collision of the particles.

7. A sensor as in claim 1 wherein the chemical species whose concentration is to be measured comprises a soluble antigen, wherein the first reagent comprises an immobilized antigen, and wherein the second reagent comprises an immobilized antibody.

8. A sensor as in claim 1 wherein the chemical species whose concentration is to be measured comprises a soluble antigen, wherein the first reagent comprises an immobilized antibody, and wherein the second reagent comprises an immobilized antigen.

9. A sensor as in claim 1 wherein the chemical species whose concentration is to be measured comprises a soluble antigen, wherein the first and second reagents comprise an immobilized antigen, and wherein the solution includes a concentration of soluble antibodies which are bindable with the antigens.

* * * * *